(12) United States Patent
King et al.

(10) Patent No.: US 11,058,435 B2
(45) Date of Patent: *Jul. 13, 2021

(54) POWERED SURGICAL DEVICE

(71) Applicants: Eugene T. King, Aquebogue, NY (US); John M. R. Fitzgerald, East Setauket, NY (US); Greg Unmann, Hawthorne, NY (US); Peter J. Esser, Alexandria, VA (US)

(72) Inventors: Eugene T. King, Aquebogue, NY (US); John M. R. Fitzgerald, East Setauket, NY (US); Greg Unmann, Hawthorne, NY (US); Peter J. Esser, Alexandria, VA (US)

(73) Assignee: TAUTOG, LLC, Aquebogue, NY (US)

( * ) Notice: Subject to any disclaimer, the term of this patent is extended or adjusted under 35 U.S.C. 154(b) by 97 days.

This patent is subject to a terminal disclaimer.

(21) Appl. No.: 16/375,446

(22) Filed: Apr. 4, 2019

(65) Prior Publication Data
US 2019/0231366 A1 Aug. 1, 2019

Related U.S. Application Data

(63) Continuation of application No. 15/807,550, filed on Nov. 8, 2017, now Pat. No. 10,292,714.

(60) Provisional application No. 62/419,170, filed on Nov. 8, 2016.

(51) Int. Cl.
| A61B 17/16 | (2006.01) |
| A61B 17/32 | (2006.01) |
| A61B 90/00 | (2016.01) |
| A61B 17/00 | (2006.01) |

(52) U.S. Cl.
CPC ...... *A61B 17/1604* (2013.01); *A61B 17/1617* (2013.01); *A61B 17/1624* (2013.01); *A61B 17/1628* (2013.01); *A61B 17/1671* (2013.01); *A61B 17/32002* (2013.01); *A61B 17/162* (2013.01); *A61B 17/1635* (2013.01); *A61B 2017/0023* (2013.01); *A61B 2017/0046* (2013.01); *A61B 2017/00296* (2013.01); *A61B 2017/00407* (2013.01); *A61B 2017/00424* (2013.01); *A61B 2017/00477* (2013.01); *A61B 2017/320032* (2013.01); *A61B 2090/034* (2016.02); *A61B 2090/036* (2016.02);
(Continued)

(58) Field of Classification Search
CPC ............ A61B 17/1604; A61B 17/1606; A61B 17/1608; A61B 17/1611; A61B 17/1613; A61B 17/1615; A61B 17/1617; A61B 17/162; A61B 17/1622; A61B 17/1624; A61B 17/1626; A61B 17/1628; A61B 17/1644
USPC .......................................................... 606/83
See application file for complete search history.

(56) References Cited

U.S. PATENT DOCUMENTS

| 5,620,415 | A | * | 4/1997 | Lucey | ................. | A61B 17/1608 604/22 |
| 6,575,978 | B2 | * | 6/2003 | Peterson | ............ | A61B 17/1604 606/171 |

(Continued)

*Primary Examiner* — Eric S Gibson
(74) *Attorney, Agent, or Firm* — Hunton Andrews Kurth LLP (57) ABSTRACT

A surgical device incorporating a powered rotary cutting tool having a protective distal foot plate which protects against injuring non-target tissue enabling the rapid and safe removal of specifically-targeted bone, cartilage, and soft tissue.

8 Claims, 9 Drawing Sheets

(52) U.S. Cl.
CPC . *A61B 2090/0813* (2016.02); *A61B 2217/005* (2013.01); *A61B 2217/007* (2013.01)

(56) References Cited

U.S. PATENT DOCUMENTS

| | | | | |
|---|---|---|---|---|
| 8,273,087 B2* | 9/2012 | Kimura | ......... | A61B 17/320068 606/79 |
| 8,864,766 B2 | 10/2014 | Weaver | | |
| 10,292,714 B2* | 5/2019 | King | ................. | A61B 17/1671 |
| 2004/0102783 A1* | 5/2004 | Sutterlin, III | ...... | A61B 17/1622 606/80 |
| 2006/0248988 A1* | 11/2006 | Bennett | ............. | A61B 17/1624 81/62 |
| 2007/0265633 A1* | 11/2007 | Moon | ............ | A61B 17/320783 606/83 |
| 2008/0086133 A1* | 4/2008 | Kuslich | ............. | A61B 17/7098 606/250 |
| 2010/0100098 A1* | 4/2010 | Norton | ............... | A61B 17/1671 606/80 |
| 2010/0178557 A1 | 7/2010 | Husted | | |
| 2010/0179557 A1* | 7/2010 | Husted | ............ | A61B 17/32002 606/83 |
| 2011/0190803 A1* | 8/2011 | To | .................... | A61B 17/32002 606/180 |
| 2011/0224654 A1* | 9/2011 | Schulz | ............... | A61B 17/1626 606/1 |
| 2013/0023882 A1* | 1/2013 | Fabro | ................... | A61B 17/295 606/80 |
| 2013/0150861 A1* | 6/2013 | Agbodoe | ........... | A61B 17/1608 606/83 |
| 2013/0172895 A1* | 7/2013 | Wallace | ............. | A61B 17/1615 606/83 |
| 2013/0172985 A1* | 7/2013 | Prestwich | ............. | A61L 27/222 623/1.41 |
| 2013/3172895 | 7/2013 | Wallace et al. | | |
| 2014/0025079 A1* | 1/2014 | Tornier | ............... | A61B 17/1617 606/83 |
| 2015/0157387 A1* | 6/2015 | Ou Yang | ........... | A61B 18/1206 606/34 |
| 2018/0214162 A1* | 8/2018 | King | .................. | A61B 17/1671 |
| 2019/0231366 A1* | 8/2019 | King | .................. | A61B 17/1604 |

* cited by examiner

POWERED SURGICAL DEVICE

CROSS REFERENCE TO RELATED APPLICATIONS

The present application is a continuation of application Ser. No. 15/807,550 filed on Nov. 8, 2017, which claims priority from provisional application 62/419,170 filed on Nov. 8, 2016, which are incorporated herein by reference herein in their entireties.

TECHNICAL FIELD

The present invention relates generally to surgical instruments and, more particularly, to improved rongeur-type instruments for cutting or sampling bone, cartilage and soft tissue.

BACKGROUND OF THE INVENTION

A rongeur is a robust surgical instrument with a sharp-edged, scoop-shaped tip, used for gouging out bone. A rongeur can be used to open a window in bone, often in the skull. It is used in neurosurgery, podiatric surgery, and orthopedic surgery to expose areas for operation. Other common applications for more specialized types of rongeurs, such as the Kerrison type, include spinal procedures. Common diagnoses for which surgeries involving a rongeur include spinal stenosis, spinal tumors, degenerative disk disease, and herniated disks.

Spinal surgery and neurosurgery typically require the surgeon to remove tissue such as bone and ligament ("target tissue") to gain access to underlying tissue such as dura, nerve roots, intervertebral disc, spinal cord, and brain ("non-target tissue") so that the intended surgery can then be performed. As an example, one very common procedure that focuses on discrete elements of the foregoing is a laminectomy in the lumbar, thoracic, or cervical spine, a surgical operation to alleviate a condition known as spinal stenosis. In a laminectomy, a surgeon removes a portion of the vertebrae known as the lamina, usually to give access to the spinal cord or to relieve pressure on nerves. Currently, in the case of highly complex procedures such as a laminectomy, it is common practice for surgeons to employ two sequential methods to achieve removal of target tissue. Generally, a surgeon will first utilize hand-held powered drills or burrs to rapidly remove relatively easily accessible target tissue. Subsequently, because of the risk of potential damage to deeper underlying non-target tissue by a rapidly rotating drill or burr, a manual, unpowered surgical tool known as a rongeur is then applied to remove residual target tissue at a much slower rate. This is done to ensure precise removal of the remaining target tissue, given that the rongeur provides greater precision and control and protection of non-target tissue because of several design features inherent to the conventional rongeur.

The surgery employing the rongeur is performed under constant visualization. Importantly, the component of a conventional rongeur which removes the target tissue is precisely applied via a sliding mechanism, sometimes referred to as a shuttle mechanism, actuated by a trigger or moving handle portion and terminating in a blade or punch mechanism. Additionally, the rongeur includes a protective distal or terminal portion, commonly referred to as a foot plate, that is positioned between target and non-target tissue. This design aspect of a rongeur helps to minimize the chance of damaging non-target tissue.

In using the typical Kerrison-type rongeur, the surgeon must carefully position the rongeur between target and non-target tissue, then squeeze the handle to remove a small piece of target tissue, usually between 2-5 millimeters. Then the entire instrument is withdrawn from the surgical site so the small piece of bone can then be manually removed from the device by the surgeon or the surgeon's assistant. The device then must carefully be reinserted between target and non-target tissue so that the above process can be repeated. Depending on the patient's condition, this process may need to be repeated many times over. In such cases, the surgical procedure is very time-consuming and results in surgical times that can take several hours. The duration of the surgery may lead to substantial bleeding and prolonged administration of general anesthesia that can be detrimental to a patient's recovery. A further downside to the use of such a rongeur is that the repetitive motion may cause hand cramping or fatigue on the part of the surgeon, which increases the risk that a patient may suffer adverse effects from inadvertent tissue removal or from unintended contact of the rongeur's cutting portion with nerve tissue. These and other issues with the traditional design have led to numerous alternative approaches to rongeur design.

Various grasping configurations, cutting or shearing designs, and variations of the two have been proposed to overcome limitations presented by state-of-the-art commercial rongeurs.

Among the designs introduced in recent years to overcome the issue of operator hand fatigue is the Aesculap KAIRison series. This device employs a pneumatic system to obviate much of the need for exerting manual leverage. A significant limitation presented by the design of the device is that it is a Kerrison-type instrument in the form of a bone punch, rather than a smoothly-operating, precisely controlled rotary tool. As in the case of all other Kerrison rongeurs, the retrieval of chipped bone or other tissue detritus is necessary after each section of tissue is ablated or otherwise detached.

Another of the designs proposed to address such concerns are U.S. Pat. No. 8,864,766 to Edgar Weaver, issued Oct. 21, 2014, which presents a Kerrison rongeur employing a bypasss-cut type shearing mechanism, for specific cutting and sampling bone, cartilage and soft tissue. One significant limitation of this design is that it will not reliably remove bone or soft tissue with a high degree of precision, due to the broad range of action, or throw, of the cutting elements.

Publication US 20040102783, attributed to Sutterlin et al, discloses a Powered Kerrison-like Rongeur system. The device incorporates a powered cutting element and features a pistol-grip actuator as a design element which appears to be intended to provide an optimized ergonomic effect.

Other inventors have tried to address the issue of debris collection. For example, a number of various commercially available devices for spinal surgery incorporate integral irrigation and suction feature in tissue-removal devices. However, the combination of a powered drill and irrigation or suction mechanisms presently available all feature an inherent limitation, in that the way the irrigation, suction, or combined irrigation-suction mechanisms are attached to the devices in all cases leads to partial obstruction of the surgeon's view of the operative field.

A further limitation present in powered devices is that the operator's ability to select from a range of cutting devices is generally restricted to the limited choice presented by a single manufacturer's pre-determined selection. As such, a surgeon or medical technician must choose from what essentially amounts to a pre-packaged toolkit. No device heretofore has overcome the limitation of the operator not being able to select from a broad range of powered cutting devices which essentially snap into place and may be easily switched out for either another identical cutting tool, or replaced by another brand and design of rotary cutting tool.

As demonstrated by the foregoing, there remains a need for an improved instrument that can cut bone and tissue, such as with a power-driven, longitudinally displaceable or slideable cutting element or burr described herein to avert the problems associated with conventionally designed rongeurs. Such powered elements can include an ability to regulate cutting speed, to actuate the cutting element in such a way as to precisely deploy or retract the burr along a range of motion, and to provide irrigation as needed, thereby reducing operator fatigue and the time of the operative procedure and minimizing the risk of damage to tissue that need not and should not be removed. Additionally, it may be desirable to incorporate an optional irrigation function into such a rongeur. Embodiments of the present device meet these needs by creating a robust, easily sterilized, and highly ergonomic powered medical instrument capable of incorporating any one of a multiplicity of rotary cutting elements of various designs and manufacture, and featuring options such as irrigation, inherent safety features, and presenting the operator with the ability to remove target tissue to a degree and rate heretofore not possible.

SUMMARY OF THE INVENTION

Embodiments of the present device can provide an ergonomic, powered surgical device for safely removing bone and other tissue with a high degree of precision, concomitantly mitigating operator fatigue.

Embodiments of the present device may also provide a surgical device combining the speed of a high-speed burr or drill with the increased control and safety inherent in the above-mentioned features of the rongeur.

Embodiments of the present device may also provide an improved powered surgical device substantially similar in basic operation to a standard Kerrison rongeur with an ergonomic grip, a positive balance and tactile response, an indexable cutting element, and a cutting or ablative surface which provides for precision in the removal of target tissue.

An additional feature that can be provided in embodiments of the present device is an improved powered surgical device featuring a distinctively formed foot plate having an angled, obliquely-rounded exterior face and angled, planar inner face further defined by a central hemispherical indentation enabling positive engagement with the cutting element at the apex of the throw of the cutting element. Preferably, the interior face of the foot plate provides for improved cutting, physical ablation, or other mechanical removal by the cutting element of target tissue, whether bone, soft tissue, or other biological material, with minimal concurrent damage to other surrounding biological material, by providing increased exposure of the cutting element to target tissue. The angled, obliquely-rounded exterior face presents a smooth profile towards the target tissue to make tissue dissection quite easy, with the instrument providing functionalities of both a cutting tool and dissecting tool.

Another feature found in embodiments of the present device is to provide an improved surgical device with the ability to maintain a relatively static position in relation to the operative site. Preferably, the device need not be removed or repositioned as frequently as a typical rongeur since, as in the example of a laminectomy procedure, the resulting bone powder produced by the burr or drill, unlike the chips resulting from a conventional rongeur, can typically be removed with suction or a pressurized water jet without the need to withdraw the device from the surgical field.

Certain embodiments of the device provide for the rotary cutting elements to be removably attached to the device to allow the operator to replace cutting elements as they wear and become dull, and to select from a range of different rotary cutting elements, including different manufacturer's rotary cutting elements. As such, a surgeon or medical technician may employ a wide selection of powered cutting elements.

Certain embodiments of the present device feature a handle-mounted drill or burr which may be selected by the operator from a variety of types, including but not limited to standard flat-end burrs to ball mill burrs to a spherical burr, actuated by a trigger, providing a more precise way for a surgeon to remove bone or other target tissue. Preferably, the device operator, typically a surgeon, can apply varying finger pressure to selectively actuate a trigger to control the speed of the device.

Another objective of the present invention is to further enhance patient safety by permitting rapid change of cutting elements to avoid continued use of the same cutting surface (as with Kerrison rongeurs) which will by default become dull from repeated use, thus leading to potential tearing of non-target tissue such as dura and nerve, ultimately causing post-operative complications such as dural tears, cerebral spinal fluid leaks, and nerve root injury.

Yet another advantage found in embodiments of the present device is the possibility of irrigation being substantially immediately and directly applied to the operative site. Irrigation is often desirable to minimize the production of debris such as bone dust, and to prevent heating of the bone tissue being operated upon, which otherwise could have deleterious effects on delicate nerve tissue adjacent to the bone tissue. Current best practices often involve applying irrigation manually with a bulb syringe to the operative field. This technique is not precise, and the irrigation fluid may be distributed both in the general location it is needed, as well as adjacent to the operative focal point, where the instrument is being used. The excess irrigant will typically be suctioned off the operative field by the surgeon or the assistant. The present device can incorporate a disposable, detachable irrigation conduit, supplied via an external source connected to the handle by means of a luer taper-type fitting, which automatically delivers irrigant where it is needed at the interface between burr and target tissue. The irrigant is directed from the distal end of the device at an angle that preferably assures that irrigation will be applied to where it is needed throughout the movement of the burr.

Various other modifications or features of this device may include the use of: a trocar at the distal end of the device for penetrating soft tissue, a needle, a powered drill, a suction mechanism, a powered drill in combination with a suction mechanism, a powered drill in combination with a pressurized water jet, an ultrasonic tip, a bipolar cautery element, and a laser, singly or in combination with one or more of the foregoing elements, or some combination thereof.

DETAILED DESCRIPTION

Referring now to the discussion that follows and to the drawings, the present device is shown in greater detail. Although the drawings represent some exemplary embodiments, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Figure 1:
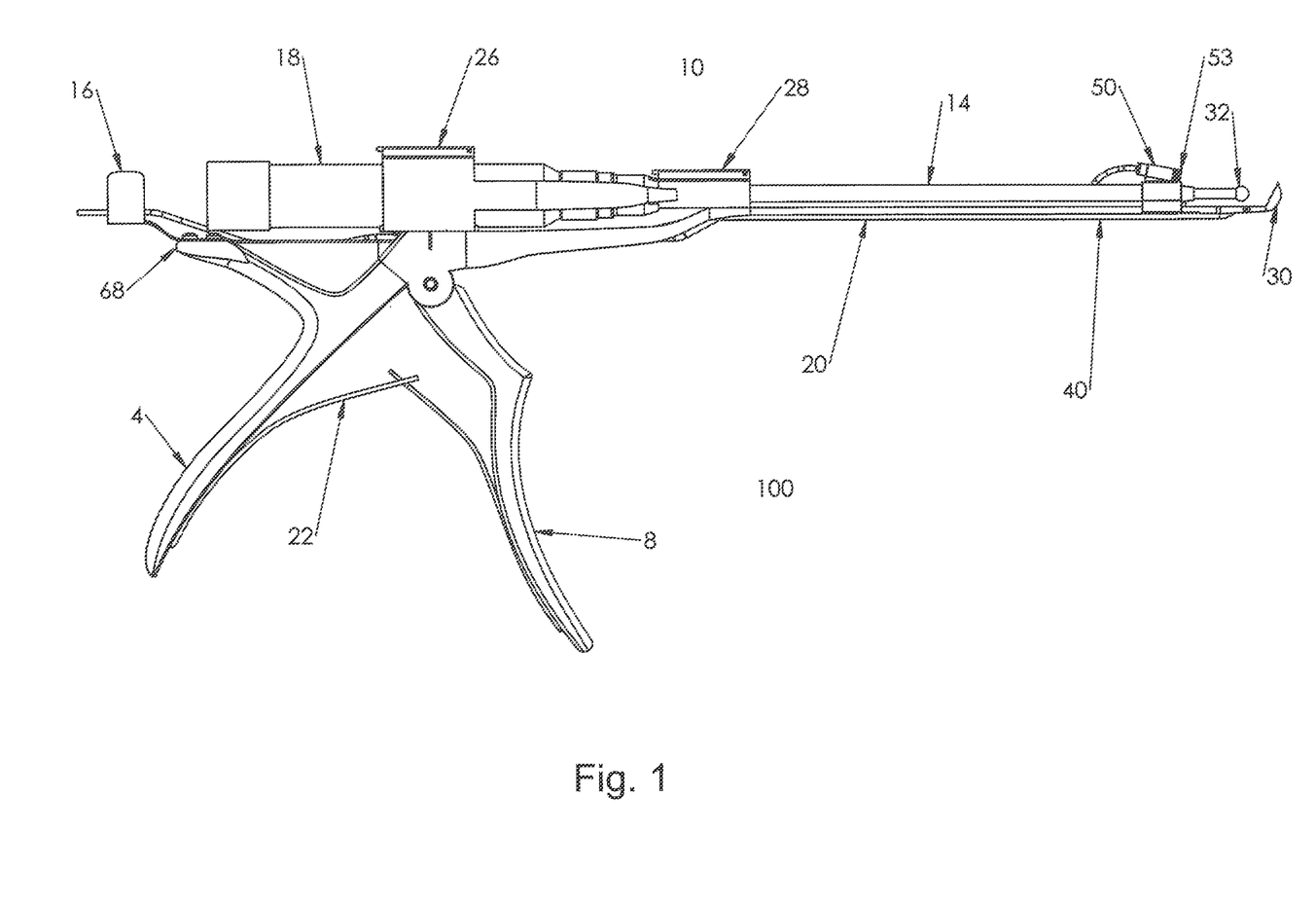
FIG. 1 is a side view of an exemplary embodiment of the present device the entirety of the inventive device.

Referring now to FIG. 1, there is shown a rongeur-type device 10 consisting of a main handle body 100 composed of interconnected handles 4 and 8, a gear 12 which extends from handle 8, actuated in relation to a biasing force imparted by elliptical springs 22 on interconnected handles 4 and 8, the biasing force being transmitted through gear 12 to rack 72 (not depicted here) to receiver carriage 20, with movable powered burr shaft 14 rotatably coupled to removable drive motor 18 and a burr 32, a power supply line (depicted in dashed lines) contained within motor umbilical retention ring 16 of receiver carriage 20, and levered shuttle clamps 26 and 28. Movable powered burr shaft 14 can travel in a reciprocating manner, proximally and distally relative to foot plate 30 and target tissue as desired by the surgeon along receiver carriage 20 in response to selectively engaging handles 4 and 8 to remove bone or soft tissue, with foot plate 30 providing protection against injury to adjacent non-target tissue.

Referring again to FIG. 1, the motor interface consists of removable drive motor 18 being coupled to the device by insertion into receiver carriage 20 and secured by levered shuttle clamps 26 and 28. A cutting element interface is achieved by coupling burr 32 to the movable powered burr shaft 14 via a chuck or collet, etc. Irrigant is transmitted from the irrigant receiving port 68 at the proximal face of handle 4 to irrigation port 56 via conduit 40, and an external, removable endoscope 53 is attached to the device via u-ring 50.

Figure 2:
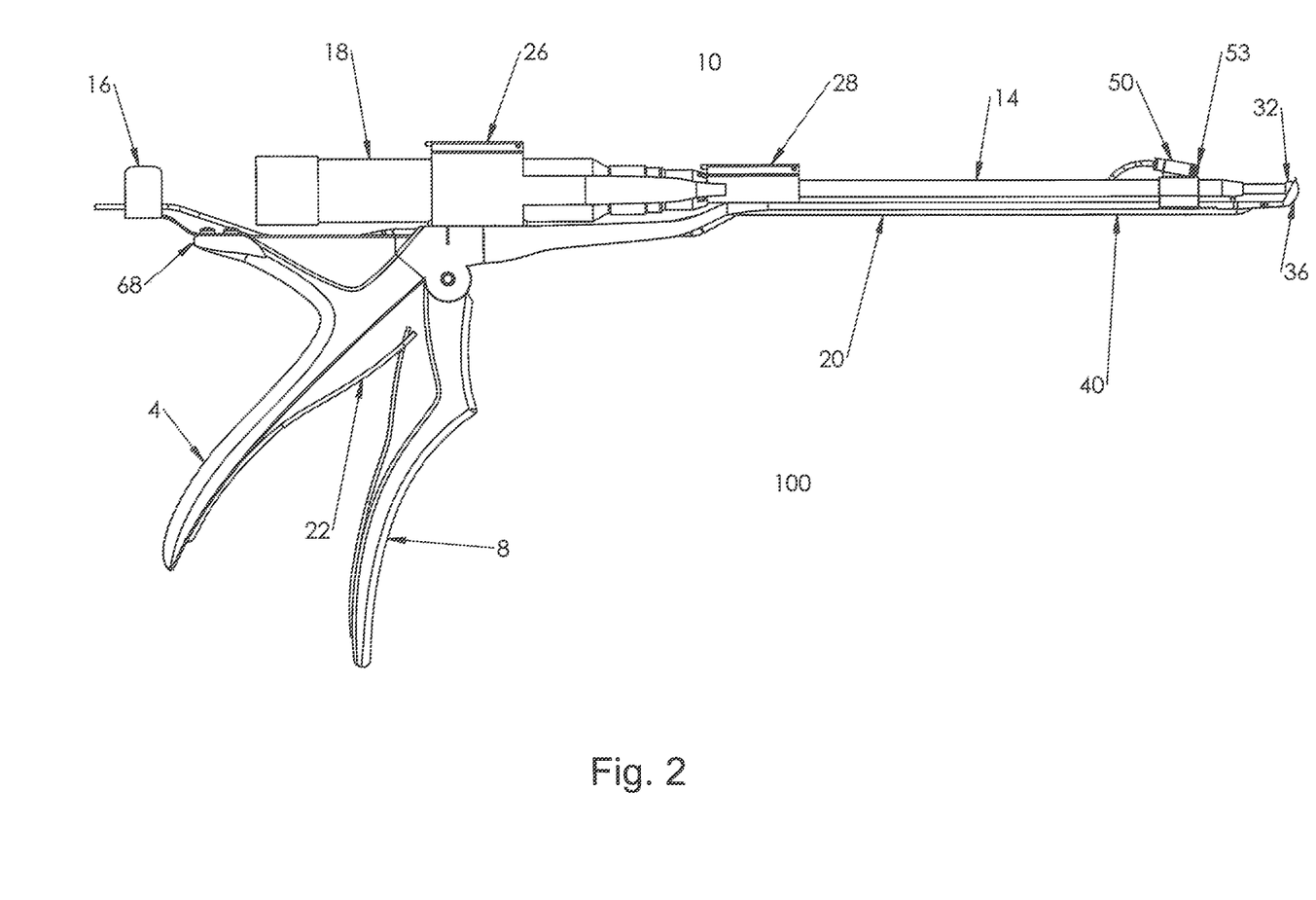
FIG. 2 is a further side view of the device of FIG. 1, showing with particularity the tissue cutting assembly fully extended.

As depicted in FIG. 2, the cutting assembly is fully extended, with handle 8 in the fully closed position relative to handle 4. The action of displacing the movable handle 8 in a fixed arc towards the fixed handle 4 leads to the forward displacement of receiver carriage 20, which leads to the extension of burr 32 along the range of the throw determined by the degree to which handles 4 and 8 are displaced relative to each other changing the relative distance between burr 32 and foot plate 30 in a highly controlled manner.

Figure 3:
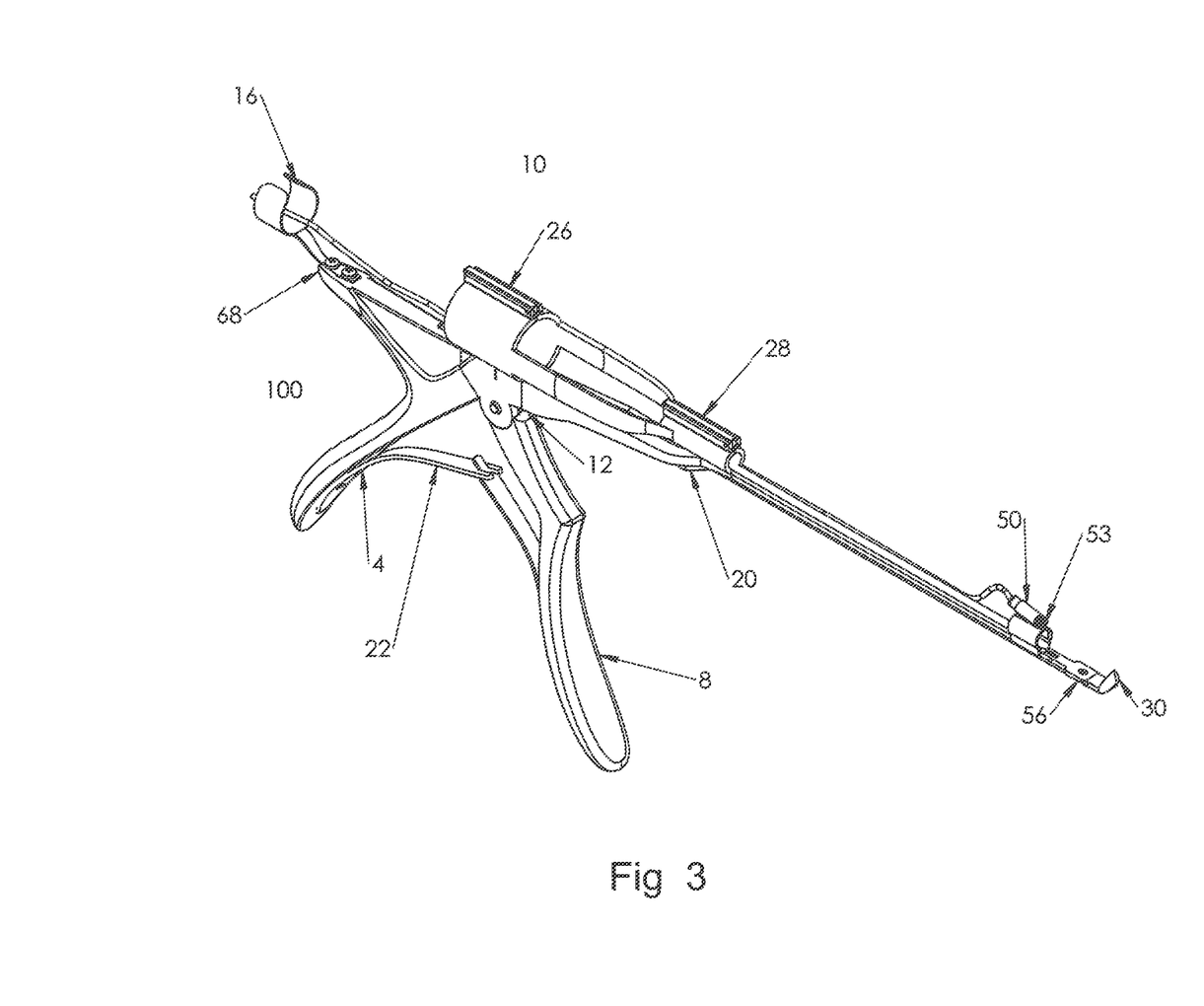
FIG. 3 is a perspective view of the device of FIG. 1.

FIG. 3 is a perspective view of the present invention 10 showing all constituent component constituted together as a complete assembly, with burr 32 in a fully retracted position and handle 8 in the fully open or extended position relative to handle 4. Presented herein is a more detailed view of levered shuttle clamps 26 and 28 which are in a closed and locked position, securing the assembly consisting of drive motor 18, movable powered burr shaft 14 and powered burr end 32 to the receiver carriage 20. U-ring 50, not referenced in this drawing, provides additional rigidity to the rongeur by positively engaging with and securing powered burr shaft 14 relative to receiver carriage 20. The positioning of irrigation port 56 is clearly visible.

Figure 4:
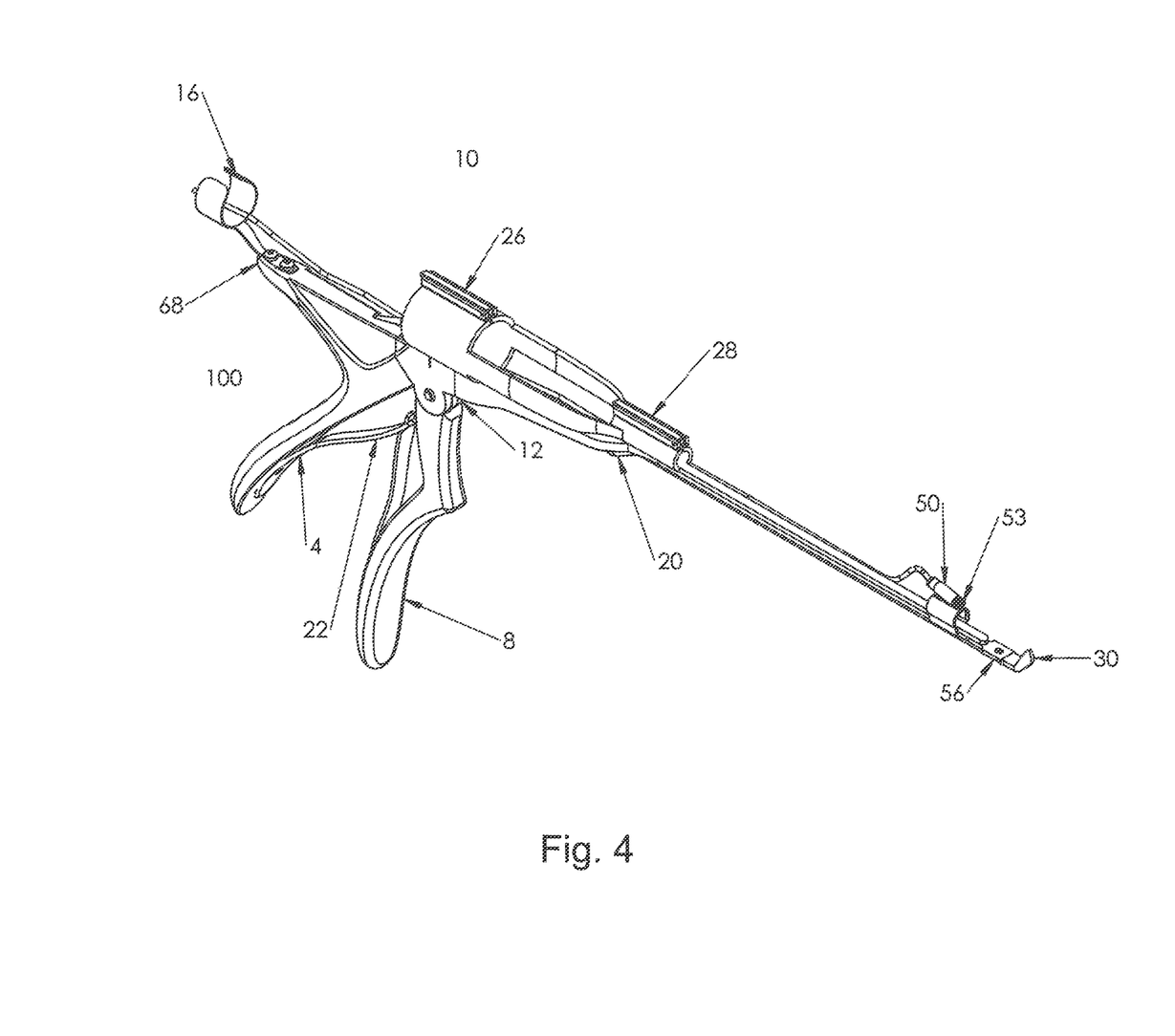
FIG. 4 is a perspective view of the present device, with burr 32 in an extended position and handle 8 retracted or closed position relative to handle 4, with burr 32 seated in a home position and with handle 8 in open position relative to handle 4, which in practice leads to a "home" position of burr 32.

FIG. 4 depicts again the complete device assembly, where the main handle body 100 is slidably connected to receiver carriage 20, with the assembly consisting of trigger-controlled drive motor 18, movable powered burr shaft 14 and powered burr end 32 as a unit inserted into the receiver carriage 20 and locked into place with levered shuttle clamps 26 and 28 and further secured by removably-affixed u-ring 50, in a manner permitting actuation of movable handle 8 relative to fixed handle 4, interconnected with gear 12, by displacing movable handle 8 along the path of an arc relative to receiver carriage 20, and engaging gear 12. Movement in the form of the engagement or release of handles 4 and 8 is transmitted by the simple linkage to the longitudinal displacement of the movable powered burr shaft 14 in receiver carriage 20, resulting in extension or retraction of burr 32. Other means of securing the assembly consisting of drive motor 18, movable powered burr shaft 14 and powered burr end 32 such as a modified circlip (not depicted) are contemplated.

Figure 5:
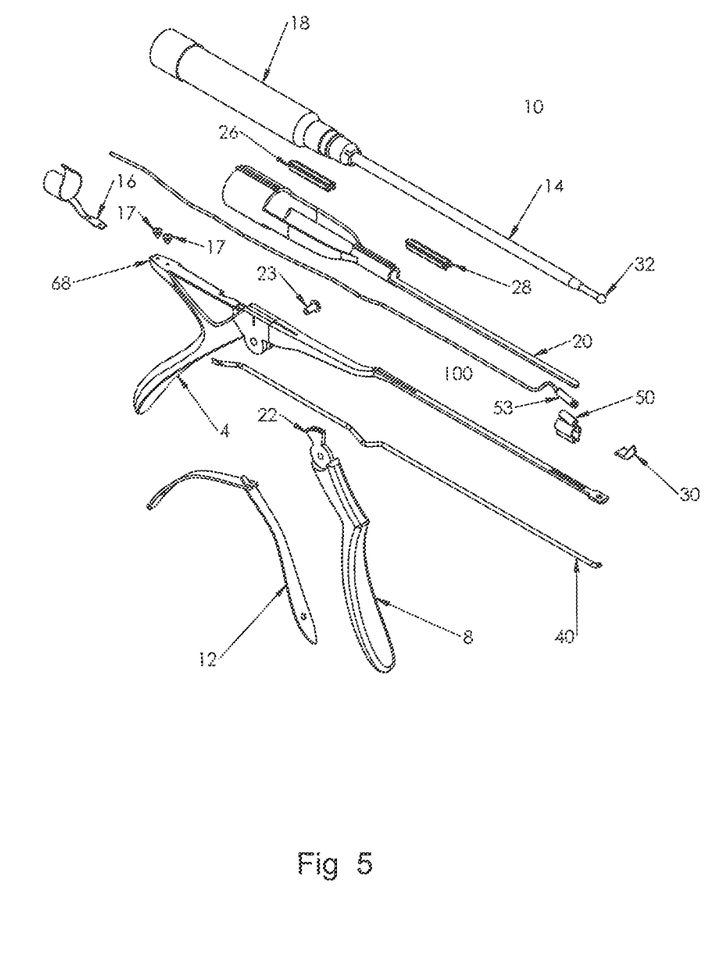
FIG. 5 is an exploded view of an embodiment of the present device.

In FIG. 5, in the exploded view the hinge pin 23 providing the interconnection of handles 4 and 8 is clearly depicted, as are the screws 17 affixing motor umbilical retention ring to handle 4.

Figure 6:
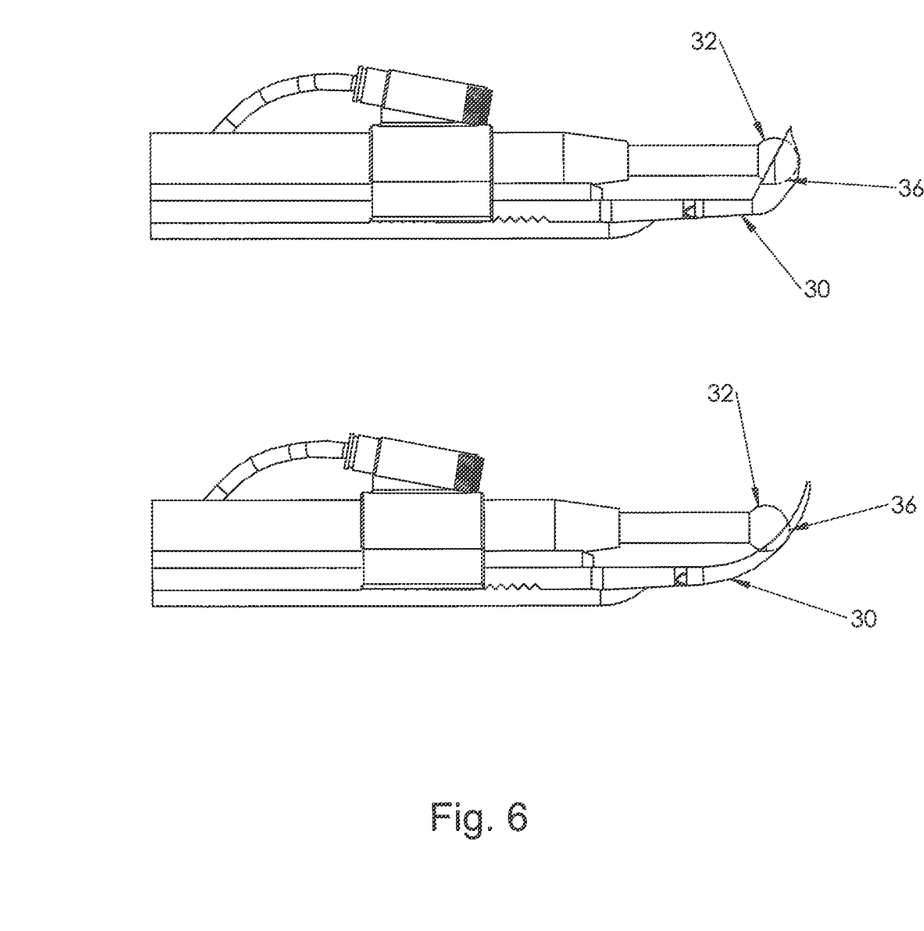
FIG. 6 is a detailed view of two variants of the foot plate 30 further illustrating an example of the interior surface of foot plate 30, depicting with a hemispherical indentation 36.

Two additional side views, as depicted in FIG. 6, show in detail two configurations of foot plate 30 with an emphasis on the interior surface of foot plate 30, depicting with particularity the hemispherical indentation 36. The hemispherical indentation 36 provides a positive receiving point for burr end 32, such that a more comprehensive removal of target tissue is achieved, with the concurrent result being that the exposed cutting face of the device is contained and secured in such a manner as to no longer present an ablative surface to non-target tissue. The distinguishing aspect between the two views is the angle and thickness of the two foot plates, with attendant differences is tissue dissection and tissue positioning outcomes.

Figure 7:
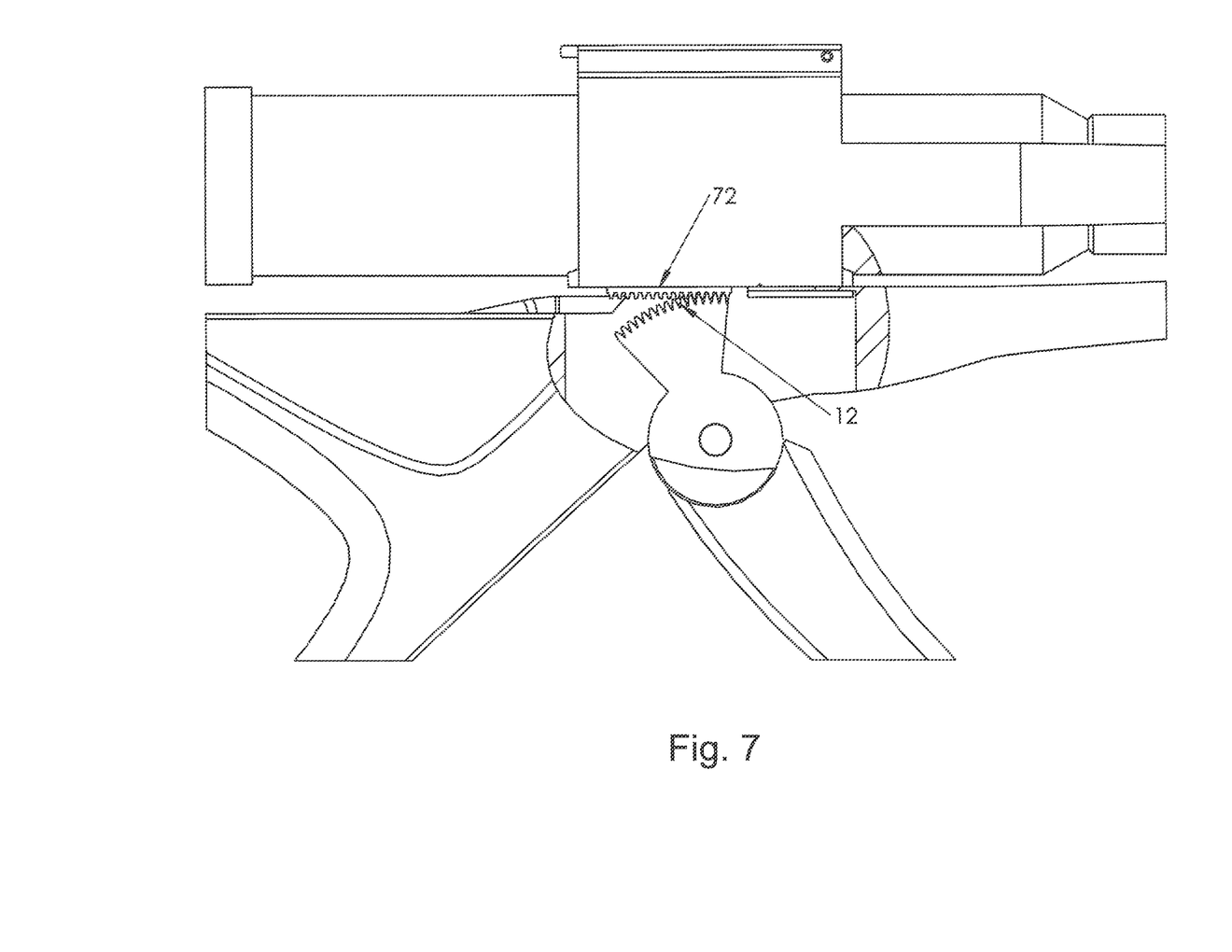
FIG. 7 is a partial side view of an embodiment of the present device showing in greater detail a drive mechanism.

In FIG. 7, the interconnection between gear 12 of handle 8 and rack 72, which provides the longitudinal displacement force for moving the cutting element, is depicted in detail.

Figure 8:
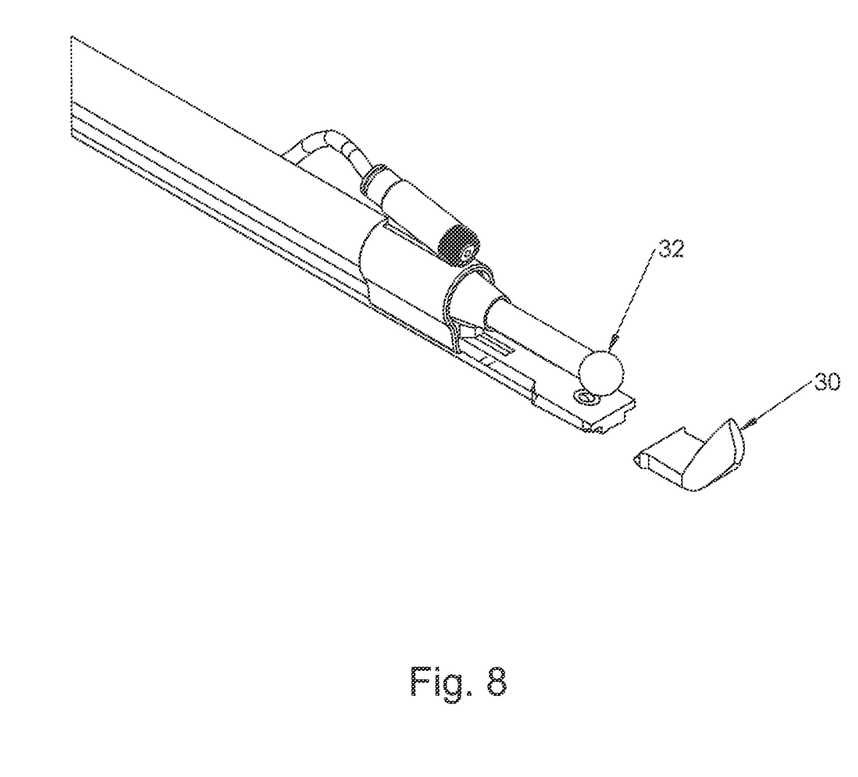
FIG. 8 is a detailed view of an embodiment of the present device more clearly presenting the removable foot plate embodiment.

FIG. 8 shows the positional interrelation between removable foot plate 30 and burr 32.

Figure 9:
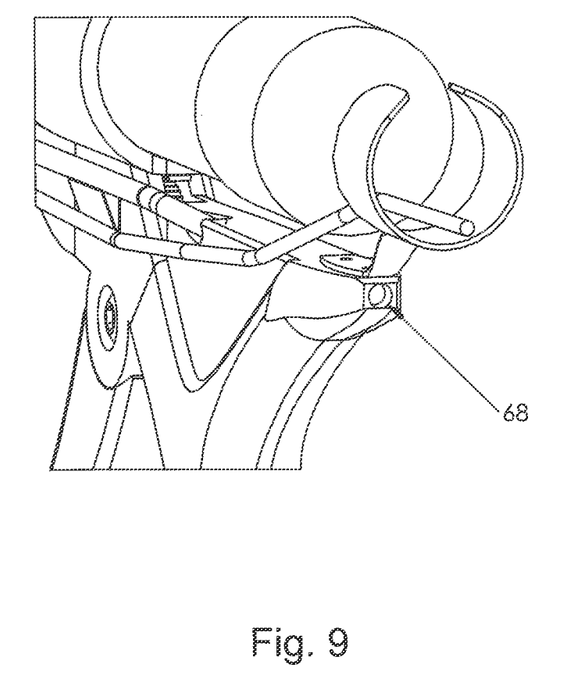
FIG. 9 is an elevation view of an embodiment of the present device depicting a point of attachment for a supply line.

FIG. 9 depicts the irrigation interface created by an irrigant supply line (not depicted) and the luer taper-type fitting irrigant constituting receiving port 68 incorporated into handle 4.

The advantages of the present rongeur-type device include, without limitation, unique functional and ergonomic properties permitting the surgeon to perform the removal of target tissue very efficiently and with far less muscle fatigue, achieving the desirable results of a considerably shortened operative time and a greatly diminished risk of cramping. A further improvement provided is increased safety presented by the adjustable burr relative to the protective foot plate 30, affording the surgeon an ability to precisely maneuver the movable powered burr shaft 14 under direct vision, via a handle-operated feature. The rongeur-type device 10 preferably combines the benefits of the speed that is achieved with using a high-velocity movable powered burr shaft 14 driven by interchangeable motor 18 with the precision and safety features inherent to a standard, manually-operated rongeur.

A further advantage is that unlike a typical Kerrison rongeur, which must be removed from the operative field to remove the piece of bone it punches out every time the handle is depressed, the presently described rongeur-type surgical instrument may typically stay in a safe position away from the nerves, and need not be removed every time a section of bone is removed. Given that the burr of the present device produces only bone dust, which is easily suctioned away, the invention reduces operative time, with attendant diminished bleeding and anesthesia time, and decreases the chance of a nerve injury, thus providing a safer surgery for patients.

Yet another advantage is that the construction of the device permits for an endoscope of either a flexible or rigid type to be securely mounted to the device, thereby providing the surgeon with a clear view of the foot plate and tissue as it is removed. This feature negates the need for the surgeon or assistant to manually attempt to keep the surgical field in view by manually holding an endoscope. This assures a clear field of view.

Additionally, the depth of bone or other tissue removal can be precisely controlled with the novel design. Moreover, the hemispherical indentation 36 in the foot plate 30 permits the powered burr end 32 to completely remove bone if so desired. This feature also allows for the controlled dissection by the powered burr end 32 end of adherent soft tissue from the underside of bone. This is particularly advantageous in the case of spinal surgical procedures known as laminectomies, where typically instruments such as curettes or elevators are employed to clear the underside of bone of adherent dura and ligament before a Kerrison rongeur is introduced for the removal of bone. In practice, the combination of the unique design of the foot plate 30 and the powered burr end 32 permit a surgeon to more precisely and securely avoid unintentional damage to desired nerve or soft tissue which might adhere to the unseen underside of bone.

As such, the entire procedure is safer for patients, who are usually unconscious under general anesthesia throughout the surgical procedure.

It should be noted that in one embodiment, the foot plate is removable, allowing the device to function as a handle to precisely manipulate a drill, burr, or other device with the added control of a handpiece as well as the advantage of irrigation as outlined above when using the foot plate attached.

It should further be noted that in one embodiment, the foot plate is removable and replaceable with another, differently dimensioned or differently angled foot plate more suited to deeper soft tissue penetration or dissection.

The above-described embodiments are for promoting an understanding of the principles of the invention. It should nevertheless be understood that no limitation of the scope of the invention is intended, and those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A surgical instrument comprising:
   an elongate receiver carriage support having a distal end;
   a receiver carriage slidably coupled to said receiver carriage support, said receiver carriage including a rotary shaft having a cutting tool interface for removeably connecting a selected rotary cutting element having a periphery, said rotary shaft being aligned with said elongate receiver carriage support;
   an actuator engaging said receiver carriage to impart linear displacement of said receiver carriage from a first position to a second position along said receiver carriage support and towards said distal end;
   a foot plate coupled to the distal end of said elongate receiver carriage and positioned in alignment with said cutting tool interface, said foot plate defining a receiving channel which is sized and shaped to substantially conform to a size and shape of the selected rotary cutting element, said foot plate receiving said rotary cutting element and covering at least a portion of the periphery of said cutting element when said actuator is in said second position.

2. The surgical instrument of claim 1 wherein said foot plate further comprises an arcuate outer surface, said outer surface and said receiving channel defining a thickness of said footplate.

3. The surgical instrument of claim 1 further comprising an irrigation port proximate the distal end of the receiver carriage support, the irrigation port being coupled to a controllable source of irrigation fluid and being aligned to apply the irrigation fluid to the cutting element.

4. The surgical instrument of claim 1 further comprising a suction port proximate the distal end of the receiver carriage support.

5. The surgical instrument of claim 1, further comprising an endoscope interface coupled to said receiver carriage for attaching an endoscope.

6. The surgical instrument of claim 1, wherein the cutting element receiving channel of said foot plate defines a substantially hemispherically shaped channel corresponding to a contour of a substantially spherical cutting element.

7. The surgical instrument of claim 1, wherein the actuator is a manually activated handle.

8. A surgical instrument comprising:
   an elongate receiver carriage support having a distal end;
   an irrigation port proximate the distal end of the receiver carriage support;
   a suction port proximate the distal end of the receiver carriage support;
   a receiver carriage slidably coupled to said receiver carriage support, said receiver carriage including a rotary shaft having a cutting tool interface for removeably connecting a selected rotary cutting element having a periphery, said rotary shaft being aligned with said elongate receiver carriage support;
   an actuator engaging said receiver carriage to impart linear displacement of said receiver carriage from a first position to a second position along said receiver carriage support and towards said distal end;
   a foot plate coupled to the distal end of said elongate receiver carriage and positioned in alignment with said cutting tool interface, said foot plate defining a substantially hemispherically shaped receiving channel which is sized and shaped to substantially conform to a size and shape of the selected substantially spherical rotary cutting element, said foot plate receiving said rotary cutting element and covering at least a portion of the periphery of said cutting element when said actuator is in said second position.

* * * * *